United States Patent [19]

Hammar et al.

[11] Patent Number: 4,786,657
[45] Date of Patent: Nov. 22, 1988

[54] POLYURETHANES AND POLYURETHANE/POLYUREAS CROSSLINKED USING 2-GLYCERYL ACRYLATE OR 2-GLYCERYL METHACRYLATE

[75] Inventors: W. James Hammar; John S. Staral, both of St. Paul, Minn.

[73] Assignee: Minnesota Mining and Manufacturing Company, St. Paul, Minn.

[21] Appl. No.: 69,428

[22] Filed: Jul. 2, 1987

[51] Int. Cl.$^4$ ............................................. C08F 2/46
[52] U.S. Cl. ........................................ 522/90; 528/75; 528/26; 528/28; 522/148; 522/149; 522/164; 526/301; 526/302; 526/303.1
[58] Field of Search .............. 528/75, 26, 28; 522/90, 522/148, 149, 164; 526/301, 302, 303.1

[56] References Cited

U.S. PATENT DOCUMENTS 4,366,301 12/1982 Le Roy et al. ...................... 528/66
4,408,020 10/1983 Kolycheck ........................... 525/415
4,446,286 5/1984 Kolycheck et al. ................. 525/455
4,467,078 8/1984 Kolycheck et al. ................. 525/455
4,478,504 3/1986 Hammar ............................. 560/112
4,598,009 7/1986 Christie et al. ..................... 428/172
4,684,538 8/1987 Klemarczyk ........................ 528/28

OTHER PUBLICATIONS

Russian publication (Chem. Absts. No. CA90(14): 104,388), Vysokomol. Soedin., Ser. B, 20(10), 777–779, Ezrielev and Arbuzova.

Primary Examiner—Melvyn I. Marquis
Attorney, Agent, or Firm—Donald M. Sell; Lorraine R. Sherman

[57] ABSTRACT

A crosslinkable polyurethane or polyurethane/polyurea comprises the reaction product of a composition comprising a macrodiol or macrodiamine, 2-glyceryl acrylate or 2-glyceryl methacrylate, a diisocyanate, and optionally a small glycol or small diamine as chain extender. The performance properties of the polyurethanes and polyurethane/polyureas can be controlled by adjustment of the crosslink level and/or curing parameters.

30 Claims, No Drawings

POLYURETHANES AND POLYURETHANE/POLYUREAS CROSSLINKED USING 2-GLYCERYL ACRYLATE OR 2-GLYCERYL METHACRYLATE

TECHNICAL FIELD

The present invention relates to novel crosslinkable and crosslinked polyurethanes or polyurethane/polyureas and methods for their preparation and to articles made from the polymers. In another aspect, the invention relates to controlling the performance properties of the polymeric articles by adjustment of the crosslink level and/or curing parameters.

BACKGROUND OF THE INVENTION

Polyurethanes and polyurethane/polyureas are widely employed as high performance engineering materials in a variety of industrial applications; the mechanical and physical properties for which they are considered the materials of choice in such applications are often directly relatable to the block-copolymer nature of these materials. The polyurethanes and polyurethane/polyureas are composed of blocks or segments of chemically different units. At service temperatures, one of the segments is generally viscous or rubbery ("soft" segment) while the other is of a glassy or semicrystalline nature ("hard" segment). Due to incompatabilities between the "hard" and "soft" components, these materials may undergo phase-separation in the solid-state resulting in the formation of a "soft" and "hard" two-phase microstructure. This phase separation observed in polymer systems leads to enhanced mechanical properties, such as tensile and modulus. In addition, the properties, service temperature limits, and utilities of such materials may often be improved or extended in industrial applications by crosslinking the polymer either thermally (with or without thermal initiator additives) or via ultraviolet light, gamma or accelerated electron beam radiation.

U.S. Pat. No. 4,366,301 describes the use of the acrylic or methacrylic acid ester of a trihydric alcohol, preferably the known compound 2,3-dihydroxypropyl acrylate (also called 1-glyceryl acrylate), as the unsaturated diol for crosslinking thermoplastic polyurethane resins containing ethylenic side groups.

U.S. Pat. No. 4,408,020 describes polyurethanes prepared from hydroxyl terminated polymers, organic diisocyanates and polyethers having terminal hydroxyl and unsaturated groups or terminal hydroxyl and pendent unsaturated groups. These polyurethanes are electron beam cured to form useful binder systems for magnetic tape.

U.S. Pat. No. 4,446,286 describes improved electron beam curable polyurethane compounds obtained from a mixture of (1) polyurethanes prepared from polymeric polyols, organic diisocyanates and polyethers having terminal hydroxyl and unsaturated groups or terminal hydroxyl and pendent unsaturated groups and (2) acrylate or alkacrylate terminated polyurethanes prepared by reacting isocyanate terminated prepolymers of hydroxyl terminated polymers with hydroxyl terminated acrylates or alkylacrylates.

U.S. Pat. No. 4,467,078 describes improved electron beam curable polyurethane compounds having a greater range in degree of cure, consequently providing systems with a greater range of hardness (modulus) for use in binder systems for magnetic tape.

A Russian publication (Chem.Absts.No. CA90(14):104388) Vysokomol. Soedin., Ser. B, 20(10),777–9 by Ezrielev and Arbuzova, describes linear polymers of glycerol monomethacrylate(PMMG) obtained from isopropylideneglyceryl methacrylate. The ketonic protection was removed from the monomer units by either acid hydrolysis, or preferentially, by alcoholysis and the resultant polymer was used to prepare hydrogels. Ezrielev and Arbuzova did not teach or suggest the use of 2-glyceryl methacrylate monomer.

The preparation of readily solvolyzable, polymerizable acrylate and methacrylate monomers and polymers is described in U.S. Pat. No. 4,578,504. One of the classes of monomers disclosed is represented by the formula:

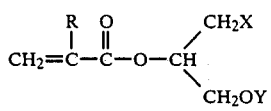

wherein R is hydrogen or methyl

X is fluoro, chloro, bromo, iodo, hydroxyl, perfluoroalkylsulfonoxy of one to three carbon atoms or perfluoroacyloxy of one to three carbon atoms, benzoyloxy, and trichloroacetoxy;

Y is trichloroacetyl, perfluoroacyl of the formula

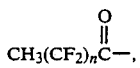

trialkylsilyl of the formula $$[CH_3(CH_2)_m]_3Si-,$$

or hydrogen. The monomer wherein X and/or -OY is hydroxy is obtained by hydrolysis of compounds wherein X is perfluoroalkylsulfonoxy, perhaloacyloxy, benzoyloxy, or trialkylsiloxy.

SUMMARY OF THE INVENTION

Briefly, the present invention provides a crosslinkable polyurethane or polyurethane/polyurea comprising the reaction product of a composition comprising a macrodiol or macrodiamine, 2-glyceryl acrylate or 2-glyceryl methacrylate (also called 1,3-dihydroxy-2-propyl (meth)acrylate), a diisocyanate, and, optionally a small glycol or diamine.

In another aspect, a crosslinked polyurethane or polyurethane/polyurea is provided by thermal, radiation, or electron beam cure of the crosslinkable polyurethanes or polyurethane/polyureas of the invention. Crosslinkable polyurethanes or polyurethane/polyureas of the invention generally have number average molecular weights in the range of 10,000 to 400,000.

The present invention provides the design, synthesis and incorporation of acrylates and methacrylates into crosslinkable polyurethanes or polyurethane/polyureas which can be made into articles of manufacture and which allow optimization of the performance characteristics of such articles via adjustment of the type or ratios of reactants and adjustment of the level of crosslinking in the polyurethane or polyurethane/polyurea.

The present invention provides a controllable method for adjustment of crosslinking of polyurethanes and polyurethane/polyureas. This is accomplished utilizing 2-glyceryl acrylate or 2-glyceryl methacrylate, represented by formula I,

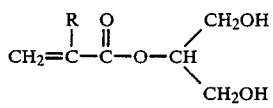

wherein R is hydrogen or methyl, as a thermal, ultraviolet light, gamma radiation, or electron beam crosslinkable chain extender in polyurethanes or polyurethane/polyureas which contain at least one of polyether, polyester, and polysiloxane segments.

In this application:

"(meth)acrylate" means acrylate or methacrylate;

"chain extender" or "small glycol" or "small diamine" means a low number average molecular weight (<400) diol or diamine, respectively;

"macrodiol" or "macrodiamine" means a high number average molecular weight ($\geq 400$) diol or diamine, respectively.

DETAILED DESCRIPTION OF THE INVENTION

The novel polyurethanes or polyurethane/polyureas of the invention and the methods for their preparation utilize 2-glyceryl acrylate or 2-glyceryl methacrylate (formula I) as a chain extender to allow selective and controllable crosslinking of the resultant polymer. The polymerizable compositions also contain macrodiols which may be, for example, polyether or polyester glycols or silicone carbinols or macrodiamines (formula II), which may be, for example, polyether diamines, or polydimethylsiloxane diamines. In addition, other small glycols or diamines (formula III) can be present, optionally, as additional chain extenders. Finally, organic diisocyanates are present in the polymerizable composition. Upon application of heat the linear polyurethanes and polyurethane/polyureas are provided. Application of additional energy, either thermal (with or without a thermal initiator) or ultraviolet light, gamma radiation or electron beam radiation, converts the linear polyurethane or polyurethane/polyurea into a crosslinked network. The crosslinked polyurethane or polyurethane/polyurea polymers of the invention are useful for preparing materials of use in areas including flexible magnetic recording media binders, biomaterials, wound dressing materials, membranes, membrane applications (waterproof fabric treatments), and protective coatings.

The method of the invention is shown in the flow chart below:

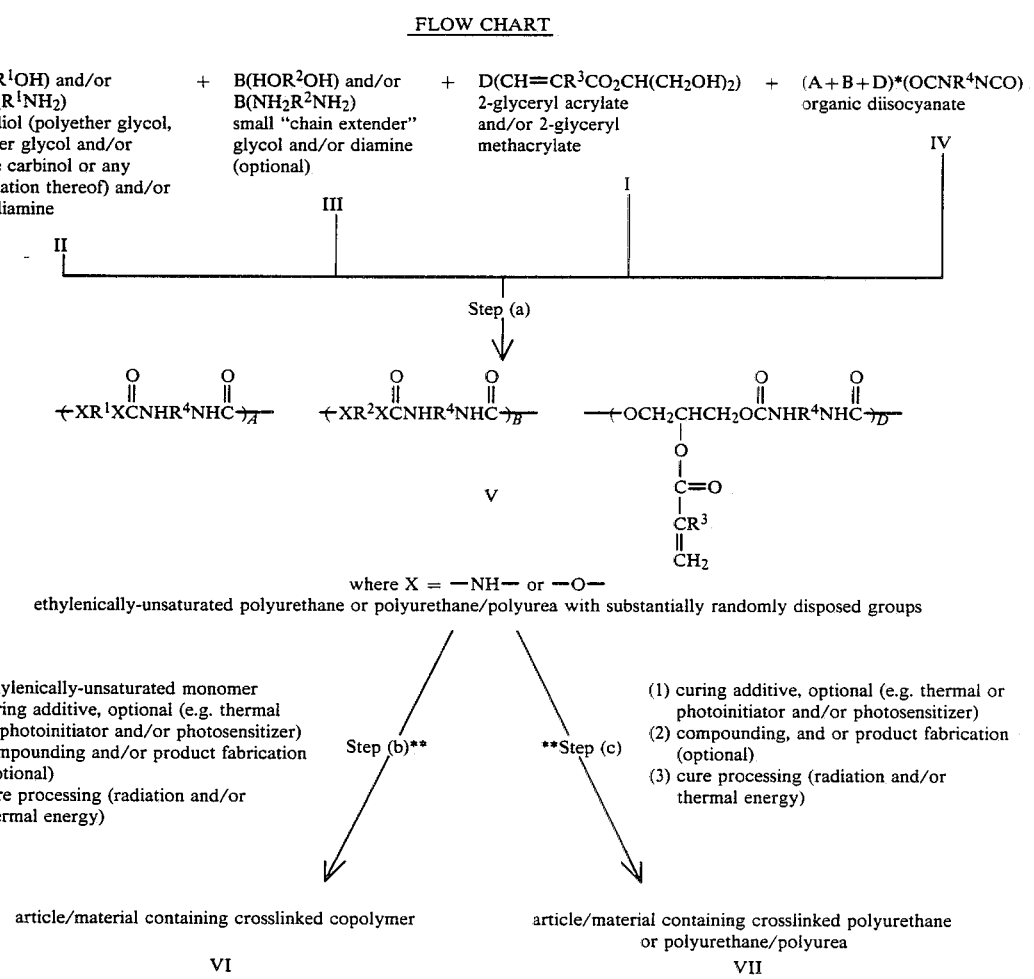

-continued
FLOW CHART

R³   substituted-arylene or any combination thereof
     may be hydrogen and/or methyl
Possible polymer end groups include

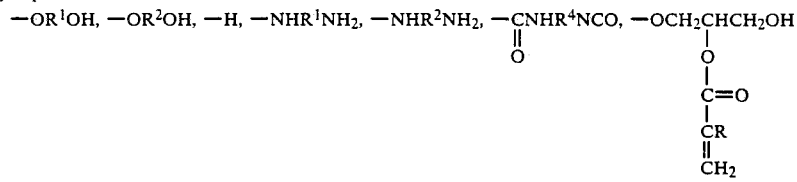

*The sum of A, B, D denotes the total number of OH and/or NH₂ equivalents; the total number of NCO equivalents may be modified from the quantity (A+B+D) depicted above, i.e. these can be up to 10 mole percent excess NCO equivalents.
**The order of the sub-steps may be modified.

The required 2-glyceryl(meth)acrylate chain extender (formula I) used in the present invention is incorporated in the range of 0.001 to 10 moles per mole macrodiol or macrodiamine in the composition.

Representative polyether glycol reactants of formula II, also termed poly(alkylene oxides), are essentially linear hydroxyl containing compounds, preferably hydroxy terminated, having ether linkages as the major linkage joining carbon atoms. The molecular weights may vary between about 400 and 40,000, and preferably are about 1,000 to 4,000 for use in this invention. Examples of polyether glycols include hydroxyl terminated poly(propylene oxide), hydroxyl terminated poly(tetramethylene oxide), hydroxyl terminated poly(trimethylene oxide), hydroxyl terminated poly(hexamethylene oxide), hydroxyl terminated poly(ethylene oxide), and the like, of the formula HO[(CH$_2$)$_n$O]$_x$H wherein n is an integer from 2 to 6 and x is an integer from 5 to 600, and alkyl substituted types such as hydroxyl terminated poly(1,2-propylene oxides), tetrahydrofuran and ethylene oxide copolyethers, and the like.

Representative polyester glycol reactants of formula II include linear hydroxyl containing carboxylic acid polyesters, preferably hydroxy terminated, having molecular weights between about 400 and 10,000, and preferably about 1,000 to 4,000. The polyesters utilized include those prepared by the polymerization of esters of aliphatic dicarboxylic acids including, for example, adipic, succinic, pimelic, suberic, azelaic, sebacic and the like or their anhydrides. Aromatic dicarboxylic acids or their anhydrides or mixtures of aliphatic and aromatic dicarboxylic acids or their anhydrides may be used. Useful acids include aliphatic dicarboxylic acids of the formula HOOC—R—COOH where R is an alkylene radical containing 1 to 10 carbon atoms, preferably 4 to 6 carbon atoms. The phthalic acids and their anhydrides are also useful. The glycols used in the preparation of the polyesters by reaction with the dicarboxylic acids are normally aliphatic diols containing between 2 and 10 carbon atoms, usually 2 to 6 carbon atoms, such as ethylene diol, propanediol, butanediol, hexamethylene diol, decamethylene diol, 2-ethylhexanediol, 1,6-neopentyl diol and the like. Representative polyester glycols may also include materials such as polycaprolactone diols.

Another macrodiol of formula II which may be used in the present invention is a silicone carbinol having the structure

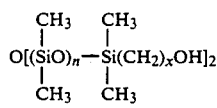

where n is 2 to 800 and
x=3 to 11.

Macrodiamines preferably have the general structure

NH$_2$R¹NH$_2$ wherein R¹ is as previously defined, preferably

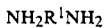

wherein R⁵ is an alkylene unit such as —(CH$_2$)$_n$— where n=3 to 11 or R⁵ may be branched alkylene unit such as

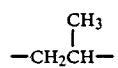

having 3 to 11 carbon atoms, and R⁶ is a polyether or polydimethylsiloxane segment. Examples of macrodiamines include poly(ethylene oxide)/poly(propylene oxide) block copolymers terminated with primary amine groups (Jeffamine ™ ED series, Jefferson Chemical Co., division of Texaco Chemical Co., Bellaire, Tex.).

Small glycols or diamines are used as chain extenders with the macrodiols or macrodiamines and the organic diisocyanate. When used these normally are aliphatic, aromatic or ether glycols, containing 2 to 20 carbon atoms. Typical glycols which may be employed include ethylene diol, propylene diol, 1,6-hexanediol, 2-ethylhexanediol, 1,6-neopentyl diol, 1,4-butanediol, 2-butene-1,4-diol, diethylene glycol and the like. Cycloaliphatic glycols such as cyclohexanedimethanol, and aromatic-aliphatic glycols such as bis-1,4-(hydroxyethoxy)benzene, may also be employed. The amount of small glycol or diamine chain extender (formula III) optionally used with the macrodiol or macrodiamine (formula II) and the diisocyanate (formula IV) may vary from 0 to 10 moles per mole of macrodiol or macrodiamine.

The organic diisocyanates (formula IV), which are reacted with the macrodiols or macrodiamines, can include, for example, alicyclic, aliphatic and aromatic diisocyanates having a molecular weight of less than 400. The diisocyanates which can be used within the scope of the invention are well known and any compounds which contain two free NCO groups can advantageously be used. Aliphatic diisocyanates include, for example, hexamethylene diisocyanate, methylenebis(4-cyclohexyl isocyanate), cyclohexyl diisocyanate, isophorone diisocyanate, etc. The aromatic diisocyanates include naphthalene-1,5-diisocyanate, diphenylmethane-4,4'-diisocyanate, toluene diisocyanate, p-phenylene diisocyanate, dibenzyl diisocyanate, diphenyl ether diisocyanate, m- and p-tetramethylxylene diisocyanate, and the like, such as are included in the general formula OCN—Ar—Y—Ar—NCO wherein Ar is cyclic, i.e. an arylene or alicyclic radical, and Y may be a carbon-to-carbon valence bond, an alkylene radical containing 1 to 5 carbon atoms, oxygen, sulfur, sulfoxide, sulfone or

where R is an alkyl radical of 1 to 5 carbon atoms.

About equimolar ratios of diisocyanate and total active hydrogens, i.e., NCO groups to -OH and/or $NH_2$ groups, are preferably used. When a small glycol or diamine chain extender is optionally used the ratio of reactants employed may be varied from about 1.1 to 15 moles of organic diisocyanate per mole total of macrodiols or macrodiamines. The amount of organic diisocyanate used is dependent on the total amount of chain extender and macrodiols or macrodiamines, and normally is a molar amount essentially equivalent to the total of these latter reactants so that there are essentially no free unreacted isocyanate groups remaining in the polymer. Where essentially equimolar amounts of isocyanate and active hydrogen groups are preferred, it will be understood that small excesses of a reactant or excess organic diisocyanate can be used in forming prepolymers. Normally, it is preferred that there should be less than 0.005 percent by weight of unreacted isocyanate groups in the crosslinkable polyurethanes or polyurethane/polyureas.

Use of 2-glyceryl methacrylate of the present invention as the crosslinkable chain extender in polyurethane or polyurethane/polyurea chemistry has the advantage over the use of 1-glyceryl methacrylate as a chain extender in that 2-glyceryl methacrylate has two primary hydroxyl groups, whereas 1-glyceryl methacrylate has one primary and one secondary alcoholic function. It is known that secondary alcohols react more slowly with isocyanates than primary alcohols. This differential in relative reactivity would be expected to cause inhomogeneities in the polymerization, insofar as the secondary alcohol would most likely be the last to react with an isocyanate end group. In addition 1-glyceryl methacrylate is quite difficult to prepare in high purity; its preparation involves acid catalyzed ring opening of glycidyl methacrylate under aqueous conditions. This leads to a transesterification reaction which produces a dimethacrylate and glycerine. In polyurethane or polyurethane/polyurea chemistry the dimethacrylate would give rise to chain termination and the glycerine would lead to crosslinked materials. The synthesis of 2-glyceryl methacrylate, the subject of U.S. Pat. No. 4,578,504, involves neutral conditions avoiding the transesterification problems.

Catalysts may be used to speed up the polyurethane or polyurethane/polyurea formation and any of those catalysts normally used by those skilled in the art may be employed. Typical catalysts include dibutyl tin dilaurate, stannous octoate and tertiary amines such as triethylamine and the like, preferably in amounts from about 0.01 to 10 phr (parts per hundred resin) and more preferably from about 0.025 to 5 phr.

Another embodiment of this invention is the ability to mix these crosslinkable polyurethanes or polyurethane/polyureas with ethylenically-unsaturated materials (preferably vinyl compounds such as acrylate or methacrylate monomers, oligomers, or polymers), in an amount ranging from 0 to 95 percent by weight, to prepare crosslinkable systems which can provide crosslinked copolymers following curing of the mixture. Acrylate monomers may consist of monoacrylates, diacrylates, triacrylates and oligomeric acrylates and diacrylates; likewise, methacrylate monomers may consist of monomethyacrylates, dimethacrylates, trimethacrylates and oligomeric methacrylates and dimethacrylates. The oligomeric mono-, di-, or tri-(meth)acrylates are prepared by the reaction of (meth)acrylic acid and an oligomeric alcohol, diol, or triol.

To provide articles of the invention, the polyurethanes or polyurethane/polyureas were dissolved in organic solvents, preferably polar solvents such as tetrahydrofuran (THF), dimethylformamide, or dimethylacetamide to form preferably about 25% (15-40% can be useful) solutions. Films were prepared by solvent coating on a release paper and drying at room temperature. The film samples were then cured with electron beam radiation. For 10 megarad dosages, the films were exposed to a 150 kV beam at a rate of 7.6 meters (25 feet) per second linear speed of the film with a nitrogen purge of 0.929 square meters (10 square feet) per minute. As noted above, prior to crosslinking, the polymers can be mixed with vinyl monomers to provide, after crosslinking, novel copolymers. Although any vinyl monomer may be used, monoacrylates, monomethacrylates, diacrylates, dimethacrylates or oligomeric diacrylates or dimethacrylates are the monomers of choice. Normally the range of exposure may be from about 0.5 to less than 15 megarads, the latter dosage being sufficiently high that it often adversely effects the physical properties of the polymers. A more useful range is about 1 to 12 megarads.

In this invention, the crosslinking is controlled by the amount of 2-glyceryl (meth)acrylate, the nature and/or amount of vinyl monomer(s), the curing conditions (such as level of thermal initiator, level of UV initiator, radiation dose or dose rate), or any combination thereof. Cure is evidenced by decrease in elongation and increased modulus of elasticity of the polyurethanes or polyurethane/polyureas, as well as insolubility in solvents such as dimethylformamide, dimethylacetamide or tetrahydrofuran. Samples that have not been crosslinked or cured will normally dissolve in one of the aforementioned solvents, while crosslinked materials will, in general, only swell.

As is known in the art, during the curing process suitable additives, i.e., photoinitiators or photosensitizers, may be compounded with the polyurethane or polyurethane/polyurea materials described herein to the corresponding thermal or photochemical reactivity of such polyurethanes or polyurethane/polyureas. In the cases where such curing is initiated via a photolytic process, such additives may include photoinitiators which may be suitable for a desired application. Suitable photoinitiators include peroxides, ketones, aldehydes, alkyl halides, organometallics, disulfides, benzoin, benzil, organic polyhalides, and inorganic ions such as ferric ion complexes. Examples of typical photosensitizers which may be suitable for such applications include such materials as dyes. In the cases where it is intended that the polyurethanes or polyurethane/polyureas described herein be cured with thermal energy, thermal initiators may be compounded with the polyurethane or polyurethane/polyurea to increase the thermal reactivity of the system. Examples of such thermal initiators include peroxides such as benzoyl peroxide, disulfides, and azo compounds such as azobisisobutyrylnitrile.

The crosslinked polyurethanes or polyurethane/polyureas of the present invention can be useful as flexible magnetic recording media binders; as biomaterials, for example wound dressing films, vascular grafts, and opthalmic devices, lenses, contact lenses and corneal implants; as protective coatings such as antiscratch coatings for wood (furniture) or metal (automobiles); as a tear-resist film, e.g. laminate in glass to prevent shattering; as membranes; and as waterproof, breathable fabric treatments.

In regard to their use as magnetic recording media binders, the crosslinked polyurethanes or polyurethane/polyureas of the present invention provide integrity and durability to the magnetic media coating.

In wound healing applications, these crosslinked polyurethanes or polyurethane/polyureas provide a transparent wound dressing which exhibits increased modulus compared to dressings made from materials of uncrosslinked systems.

As a waterproof, breathable membrane, the present crosslinked system adds launderability and dry cleanability to the final fabric/polymer composite.

As a protective coating on, for example, wood or metal, the polymers and copolymers of the invention can provide abrasion resistant materials. The polymers and copolymers of the invention can also be useful as a laminate layer in materials such as glass.

Objects and advantages of this invention are further illustrated by the following examples, but the particular materials and amounts thereof recited in these examples, as well as other conditions and details, should not be construed to unduly limit this invention.

EXAMPLE 1

Preparation of bis(trifluoracetoxymethyl)methyl methacrylate

To a cold (0-5° C.) solution of 300g (1.43 mole) of trifluoroacetic anhydride in about 1 liter of dichloromethane was added dropwise 170g (1.2 mole) of glycidyl methacrylate and stirring continued at about 0-5° C. for approximately 1 hour after completion of the addition. The reaction mixture was then allowed to stir at ambient temperature for about 20 hours, after which time the dichloromethane was evaporated in vacuo to provide a colorless residue. The product was distilled at 70-75° C./0.3mm of mercury. Structural assignment was confirmed by infrared and nuclear magnetic resonance spectral analyses.

EXAMPLE 2

Preparation of 2-glyceryl methacrylate

Air was bubbled through a stirred solution of 1.2g of methoxyhydroquinone (MEHQ) in 4 liters of methanol to which was charged 400g of bis(trifluoroacetoxymethyl) methyl methacrylate and the resultant mixture heated to the temperature of methanol distillation. Continually replacing solvent as it was removed, the solution was heated at this temperature for about 5 hours or until no starting material was evident by nuclear magnetic resonance spectral analysis. The majority of the methanol was then removed in vacuo. Residual amounts of solvent were removed utilizing a vacuum pump, providing 165g of a colorless, viscous liquid. Structural assignment was confirmed by nuclear magnetic resonance spectral analysis.

EXAMPLES 3-6

General preparation of polyurethanes

A solution of the macrodiol, the diisocyanate and the dibutyl tin dilaurate catalyst was refluxed in tetrahydrofuran for 3 hours. Then chain extender(s) dissolved in tetrahydrofuran was (were) added dropwise following the disappearance of the isocyanate absorption band in the infrared spectrum. The ratio of macrodiol/diisocyanate/chain extender(s) was 1/2/1. When the reaction was complete, thin film samples were prepared by solvent coating the thick polymer solution onto a release liner. The films were then air dried in a hood. Physical data were recorded on films before and after crosslinking. Crosslinking was accomplished by irradiation with an electron beam at 10 Mrads utilizing 150 kV at a web speed of 7.6 meters (25 feet) per minute. Table I lists the polymers prepared and Table II lists the mechanical data obtained.

TABLE I

| | Polymers Prepared | | |
|---|---|---|---|
| Example # | Macrodiol | Diisocyanate | Chain extender(s) |
| 3 | PTMO-1,000[a] | MDI[b] | 2-GMA[c] |
| 4 | PEO-1,000[d] | $H_{12}$MDI[e] | BD[f]/2-GMA (0.95/0.05) |
| 5 | PEO-1,000 | $H_{12}$MDI | BD/2-GMA (0.9/0.1) |
| 6 | PEO-1,000 | $H_{12}$MDI | BD/2-GMA (0.5/0.5) |

[a]hydroxyl terminated poly(tetramethylene oxide) number average m. wt. approximately 1,000
[b]methylene diphenyl diisocyanate
[c]2-glyceryl methacrylate
[d]hydroxyl terminated poly(ethylene oxide) number average m. wt. approximately 1,000 (Carbowax - 1,000 TM, Union Carbide)
[e]methylene dicyclohexyl diisocyanate (Desmodur W TM, Mobay Chemical Corp.)
[f]1,4-butanediol

TABLE II

| | Mechanical Data on Polyurethanes | | |
|---|---|---|---|
| | | Stress at break | Elongation at break |
| Example # | | (psi) | M. Pascals | (%) |
| 3 | uncrosslinked | 2,600 | 17.93 | 1,100 |
|   | crosslinked | 1,100 | 7.59 | 125 |
| 4 | uncrosslinked | 670 | 4.62 | 320 |
|   | crosslinked | 880 | 6.07 | 540 |
| 5 | uncrosslinked | 530 | 3.66 | 320 |
|   | crosslinked | 760 | 5.24 | 260 |
| 6 | uncrosslinked | 330 | 2.28 | 770 |
|   | crosslinked | 830 | 5.72 | 80 |

Two thick films of the polymeric solution of EXAMPLE 6 ere made: (1) with 1% azobisisobutyrylnitrile (AIBN) added and (2) with 1% benzoyl peroxide added. Small pieces of both films were placed between polyester sheets and put in a hot press at approximately 150° C. and about 4,500 kg (5 tons) pressure on a 10.2 cm (4 inch) diameter ram for approximately 15 minutes. When a very thin film that was thermoformed from the small pieces of thick film was checked for solubility in tetrahydrofuran, both the film formed using the AIBN as a thermal initiator and the film formed using benzoyl peroxide as a thermal initiator were insoluble in tetrahydrofuran; this showed that crosslinking had been effected utilizing a thermal initiator and a hot press. This demonstrates that materials of the present invention can be used to prepare a thermoset polymer system.

EXAMPLE 7

Preparation of polyurethane and crosslinking with UV irradiation

To a solution of 3.2g (20 mmole) of 2-glyceryl methacrylate dissolved in tetrahydrofuran was added 10.0g (40 mmole) of 4,4'-diphenylmethane diisocyanate and a sufficient amount of tetrahydrofuran to provide a total volume of about 200ml. Then 4 drops of dibutyl tin dilaurate was added followed by refluxing for approximately one half hour at which time 18g of poly(tetramethylene oxide)diol(number average m. wt. approximately 1000) was added. The resultant solution was refluxed for about 2 hours at which time 1,4-butanediol dissolved in tetrahydrofuran was added in small quantities following the disappearance of the isocyanate absorption band in the infrared spectrum. The weight and number average molecular weights of the resultant material were determined via gel permeation chromatography to be 143,000 and 45,000, respectively. Portions of the thick polymer solution were coated onto a release liner and irradiated for approximately 30 minutes with an ultraviolet lamp, available from Southern New England Ultraviolet Co. (RUL 3500A); the film turned brown and was no longer soluble in tetrahydrofuran. A dilute sample of the polymer solution was coated onto a sodium chloride infrared plate and the infrared spectrum recorded. The sample was then irradiated for about 15 minutes with an ultraviolet lamp (RUL 3500A TM, Southern New England Ultraviolet Co.). The irradiated film was no longer soluble in tetrahydrofuran.

EXAMPLE 8

Preparation of poly(ethylene oxide) polyurethane

To approximately 100ml of tetrahydrofuran was added 29g (20 mmoles) of poly(ethylene oxide) diol (number average m. wt. approximately 1300-1600), 10g (40 mmoles) of 4,4'-diphenylmethane diisocyanate, followed by 4 drops of dibutyl tin dilaurate. The resultant mixture was refluxed for about 0.5 hour, after which time 2-glyceryl methacrylate (approximately 3.2g) was added until the isocyanate absorption peak in the infrared spectrum was no longer visible. Film thicknesses of 0.023 mm and 0.091 mm were prepared by knife coating on release paper and were irradiated with an electron beam [10 Mrads, 150 kV, 7.6 meters (25 feet) per minute with a nitrogen purge]. Mechanical data on the films before and after crosslinking showed a very weak polymer before crosslinking with an elongation at break of approximately 1500%, whereas after crosslinking the elongation at break was about 60±17% and the stress at break was 13.74±7.38 MPa (1993±1070 psi). This film can be used as a breathable water-repellant fabric treatment.

EXAMPLE 9

Preparation of aliphatic polyurethane

To about 150 ml of tetrahydrofuran was added 40.0g of poly(tetramethylene oxide)diol, 3.9g of 4,4'-dicyclohexylmethane diisocyanate and 5 drops of dibutyl tin dilaurate. The resultant mixture was refluxed for approximately 2.25 hours at which time 0.9g of 1,4-butanediol was added dropwise, following the isocyanate band in the infrared spectrum. An additional 0.5g of 4,4'-dicyclohexylmethane diisocyanate was added followed by the addition of 1.0g of 2-glyceryl methacrylate in tetrahydrofuran. The solution was refluxed until the isocyanate peak in the infrared spectrum was no longer evident. Thin films were provided by knife coating the polyurethane solution onto two silicone release liners; half of the films were treated with electron beam radiation [10 mrads, 150 kV voltage at 7.6 meters (25 feet) per minute with a nitrogen purge]and the remainder were left untreated. The samples which were untreated showed a stress at break of 38.48±15.92 MPa (5,580±2,308 pounds per square inch), elongation at break of 720±110%, and moisture vapor transmission of 2,805±221 grams per meter squared per day; the irradiated samples gave a stress at break value of 23.72±3.26 MPa (3,440±472 pounds per square inch), elongation at break of 400%, and moisture vapor transmission of 1672±310 grams per meter squared per day. When checked for solubility, the untreated samples were soluble in tetrahydrofuran, whereas the samples exposed to radiation (crosslinked) were insoluble in tetrahydrofuran.

EXAMPLE 10

Preparation of mixed diisocyanate polyurethane

The diol prepared in Example 2 was dissolved in tetrahydrofuran to which was added 6.7g (40 mmole) of 1,6-diisocyanatohexane and 5 drops of dibutyl tin dilaurate; the resultant mixture was refluxed for about 1 hour. Then 24.4g (40 mmole) of poly(tetramethylene oxide)diol (number average m. wt. approximately 610) in tetrahydrofuran was added, followed by approximately 1 hour of reflux at which time 10.4g (40 mmole) of 4,4'-dicyclohexylmethane diisocyanate in 40 ml of tetrahydrofuran was added at one time. The resultant solution was then refluxed for about 1 hour. Then 1.8g of 1,4-butanediol was added dropwise while monitoring the disappearance of the isocyanate band by infrared spectroscopy. The solution was stirred for about 16 hours at approximately 20° C. at which time no isocyanate absorption was evident by infrared analysis. The weight and number average molecular weights of the resultant material were determined via gel permeation chromatography to be 45,000 and 22,000, respectively. A portion of the thick polymer solution was coated onto a release liner and dried to provide an elastomeric film which was irradiated for about 20 minutes with an ultraviolet lamp (RUL 3500A) at which time the film was found to be insoluble in tetrahydrofuran. The data show that crosslinked polymer films for membrane applications can be prepared by this coating and curing process.

EXAMPLE 11

Preparation of aromatic polyurethane

A mixture of 7.0g (20 mmole) of bis(trifluoroacetoxymethyl)methyl methacrylate and 0.4g of phenothiazene in 100ml of methanol were refluxed until the volatiles were distilled off as evidenced by the disappearance of the carbonyl absorption for the trifluoroacetate by infrared analysis. During the distillation fresh methanol was added to maintain at least a 30ml volume in the reaction flask. When distillation was complete, the remaining methanol was removed by evaporation in vacuo and the residue was dissolved in tetrahydrofuran to which was added 10.0g (40 mmole) of 4,4'-diphenylmethane diisocyanate plus sufficient tetrahydrofuran to bring the total volume to about 200ml. Poly(ethylene oxide) diol (20.0g) (number average m. wt. approximately 1,000; dried at 100° C. under vacuum for about 16 hours) was added and the resultant mixture refluxed for approximately 2 hours at which time the polymer was chain extended by adding a small amount of 1,4-butanediol dropwise while following the isocyanate absorption band by infrared analysis. Portions of the polymeric solution were coated onto two release liners to give final film thicknesses (dried) of both 25.4 micrometers (1 mil) and 330 micrometers (13 mils). Both sets of samples were then irradiated with an accelerated electron beam at 10 Mrads at 7.6 meters (25 feet) per minute at voltage level of 150 kV. Additionally some of the 330 micrometer (13 mil) samples were turned over and irradiated with an accelerated electron beam at 10 Mrads at 7.6 meters (25 feet) per minute at voltage level of 200 kV. When checked for solubility, the non-irradiated (uncrosslinked) samples were soluble in tetrahydrofuran, whereas the irradiated (crosslinked) samples were insoluble in tetrahydrofuran.

EXAMPLE 12

Preparation of polyether polyurethane

A mixture of 100g (0.1 mole) of poly(ethylene oxide) diol, 52.47g (0.2 mole) of 4,4'-dicyclohexylmethane diisocyanate and 9 drops of dibutyl tin dilaurate in approximately 760ml of tetrahydrofuran were heated to reflux under a nitrogen atmosphere for about 1 hour. To this was added one half of a solution of 8.11 g (0.09 mole) of 1,4-butanediol and 1.6g (0.01 mole) of 2-glyceryl methacrylate in about 40ml of tetrahydrofuran. The remainder of the solution was added portionwise at thirty to forty-five minute intervals, monitoring the isocyanate peak in the infrared spectrum; its disappearance was evident after the addition of an additional 8 drops of 1,4-butanediol. The solution was filtered through glass wool to remove a small amount of particulate matter.

EXAMPLES 13–18

Using the method of Example 12, one of the four methacrylates listed in Table III was added to the polymeric solution before electron beam treatment. The proportions are given in Table III below. Portions of the resultant polymeric solutions (at 29.7% solids in tetrahydrofuran) were coated onto a release liner to give a final dried thickness of about 50.8 micrometers (2 mils) and one half of the samples were irradiated with an accelerated electron beam as detailed in Example 11. All the irradiated films were insoluble in tetrahydrofuran after treatment.

TABLE III

| Example # | g solution | g polymer | g methacrylate* |
|---|---|---|---|
| 13 | 23.65 | 5.42 | 0.60 CHMA |
| 14 | 24.28 | 5.56 | 0.62 HEMA |
| 15 | 26.86 | 6.15 | 0.68 EGDMA |
| 16 | 25.42 | 5.82 | 0.65 SIMA |

TABLE III-continued

| | | | |
|---|---|---|---|
| 17 | 26.84 | 6.78 | 0.75 CHMA |
| 18 | 24.43 | 6.17 | 0.69 SIMA |

| Example # | PEO*/H$_{12}$MDI*/BD*/Methacrylate (molar ratios) | | | |
|---|---|---|---|---|
| 13 | 1 | 2 | 0.9 | 0.1 |
| 14 | 1 | 2 | 0.9 | 0.1 |
| 15 | 1 | 2 | 0.9 | 0.1 |
| 16 | 1 | 2 | 0.9 | 0.1 |
| 17 | 1 | 2 | 0.5 | 0.5 |
| 18 | 1 | 2 | 0.5 | 0.5 |

*CHMA = cyclohexyl methacrylate
HEMA = 2-hydroxy ethyl methacrylate
EGDMA = ethylene glycol dimethacrylate
SIMA = polydimethylsiloxane dimethacrylate
PEO = hydroxyl terminated poly(ethylene oxide) (Carborwax-1,000))
H$_{12}$ MDI = methylene dicyclohexyl diisocyanate (Desmodur W)
BD = 1,4-butanediol

EXAMPLE 19

Crosslinkable silicone polyurethane

A solution of 7.8 g (30 mmoles) of methylene dicyclohexyl diisocyanate, 8.5 g (5 mmoles) of a silicone carbinol(IX),

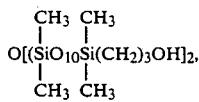

$$O[(SiO_{10}Si(CH_2)_3OH]_2,$$

with CH$_3$ groups (formula IX)

10 g (10 mmoles) of polytetramethylene glycol (molecular weight of 1,000), 100mL of tetrahydrofuran and 3 drops of dibutyl tin dilaurate was stirred at reflux of 15 hours. Then 1.6 g (10 mmoles) of 2-glyceryl methacrylate was added followed by refluxing the solution one hour. A solution of 1 g of 1,4-butanediol in 20 mL of tetrahydrofuran was added dropwise until the infrared spectra no longer showed an NCO abosrption. A portion of this polymer solution was poured onto a silicon release paper, spread to a thin film and air dried. The film was irradiated with an electron beam at 5 Mrads and 160 kV at a line speed of 7.6 m (25 feet) per minute. The irradiated film was not soluble in tetrahydrofuran or dimethyl acetamide.

EXAMPLE 20

Crosslinkable polyurethane/polyurea containing silicone

A solution of 7.8 g (30 mmoles of methylene dicyclohexyl diisocyanate, 14 g (14 mmoles) of poly(tetramethylene oxide) glycol (no. av. molecular wt. about 1000), 100 mL of tetrahydrofuran and 3 drops of dibutyl tin dilaurate was stirred at reflux for 3 hours. Then 1.6 g (10 mmoles) of 2-glyceryl methacrylate in 20 mL of tetrahydrofuran was added and the solution was refluxed an additional 40 minutes. The solution was cooled in an ice bath and 3.0 g of aminopropyl terminated polydimethylsiloxane (Petrarch Systems cat. no. PS513, viscosity 2,000 cst) was added. Then a solution of 0.3 g of ethylene diamine in 10 mL of tetrahydrofuran was added dropwise until the infrared spectrum no longer exhibited an NCO absorption. A thin film of the polymer was prepared and irradiated with 5 Mrads and 160 kV and at a line speed of 7.6 m (25 feet) per min. After irradiation the film was no longer soluble in tetrahydrofuran.

EXAMPLE 21

Crosslinkable polyurethane/polyurea containing an oligomeric diamine

A solution of 3.48 g (38.6 mmole) of 1,4-butanediol, 0.69 g (4.3 mmoles) of 2-glyceryl methacrylate, 22.5 g (85.8 mmoles) of methylene dicyclohexyl diisocyanate, 200 mL of tetrahydrofuran and 5 drops of dibutyl tin dilaurate was refluxed one hour. The solution was cooled to room temperature and a solution of a polyether diamine (Jeffamine ™ ED600 (25.73 g, 42.9 mmoles) in 50 mL of isopropyl alcohol was added until the NCO absorption in the infrared spectrum had disappeared. A thin film of this polymer was prepared and irradiated with an electron beam at 5 Mrads and 160 kV at a line speed of 7.6 m (25 feet) per minute. After this irradiation the polymer film was no longer soluble in tetrahydrofuran/isopropyl alcohol solution or dimethyl acetamide.

EXAMPLE 22

Crosslinkable polyurethane/polyurea containing ethylene diamine as a chain extender A solution of 37.5 g (37.5 mmoles, 1,000 approx. no. av. molecular weight) poly(ethylene oxide) glycol, 1.13 g (12.5 mmoles) of 1,4-butanediol, 2.00 g (12.5 mmoles) of 2-glyceryl methacrylate, 19.68 g (75.0 mmoles) methylene dicyclohexyl diisocyanate, 5 drops dibutyl tin dilaurate and 200 mL of tetrahydrofuran were refluxed three hours. The solution was cooled to room temperature and a solution of 0.75 g (12.4 mmoles) of ethylene diamine in 10 mL of isopropyl alcohol was added until there was no evidence of NCO absorption by infrared analysis. A polymer film was prepared and irradiated with an electron beam at 5 Mrads and 160 kV at a line speed of 7.6 m (25 feet) per minute. The polymer was no longer soluble in tetrahydrofuran/isopropyl alcohol mixture.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A crosslinkable polyurethane or polyurethane/polyurea comprising the reaction product of a composition comprising a macrodiol having a number average molecular weight of at least 400 or macrodiamine having a number average molecular weight of at least 400, 2-glyceryl acrylate or 2-glyceryl methacrylate, and a diisocyanate.

2. The crosslinkable polyurethane or polyurethane/polyurea according to claim 1 further comprising a small glycol having a number average molecular weight of less than 400 or small diamine having a number average molecular weight of less than 400 in the reaction composition.

3. The crosslinkable polyurethane or polyurethane/polyurea according to claim 1 wherein said composition further comprises at least one ethylenically-unsaturated monomer.

4. The crosslinkable polyurethane or polyurethane/polyurea according to claim 3 wherein said ethylenically-unsaturated monomer is an acrylate or methacrylate monomer.

5. The polyurethane or polyurethane/polyurea according to claim 1 which has been crosslinked by means of at least one of thermal energy, ultraviolet radiation, gamma radiation, or electron beam radiation.

6. The polyurethane or polyurethane/polyurea according to claim 1 wherein said macrodiamine in said composition is a polyether diamine or a polydimethylsiloxane diamine.

7. The polyurethane or polyurethane/polyurea according to claim 2 wherein said small glycol is an aliphatic, aromatic, or ether glycol containing 2 to 20 carbon atoms.

8. The polyurethane or polyurethane/polyurea according to claim 2 wherein said small diamine is an aliphatic, aromatic, or ether diamine containing 2 to 20 carbon atoms.

9. The polyurethane or polyurethane/polyurea according to claim 4 wherein the acrylate or methacrylate monomer is a mono-, di-, tri-, or oligomeric acrylate or methacrylate which is the reaction product of acrylic or methacrylic acid and an oligomeric alcohol, diol, or triol.

10. The polyurethane or polyurethane/polyurea according to claim 9 wherein said oligomeric alcohol or diol is a polyether, polyester, or polydimethylsiloxane moiety.

11. A crosslinkable polyurethane or polyurethane/polyurea having randomly disposed units of the formula

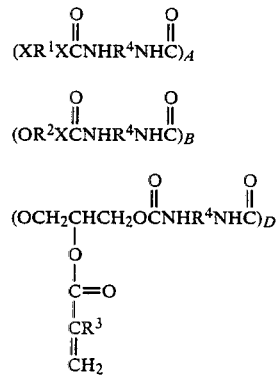

wherein:
X is —NH— or —O—,
$R^1$ is a polyether, a polyester, or a polydimethylsiloxane segment,
$R^2$ and $R^4$ independently are selected from the class consisting of alkylene, cycloalkylene, and arylene groups and combinations thereof
$R^3$ is H or $CH_3$, and
A, B, D=total number of OH and NH equivalents and the total molecular weight of the A, B, and D units is in the range of 10,000 to 400,000.

12. A method comprising the step of
(a) reacting a macrodiol having a number average molecular weight of at least 400 or macrodiamine having a number average molecular weight of at least 400, a diisocyanate, and 2-glyceryl acrylate or 2-glyceryl methacrylate to provide a crosslinkable polyurethane or polyurethane/polyurea.

13. The method according to claim 12 further comprising also reacting a small glycol having a number average molecular weight of less than 400 or small diamine having a number average molecular weight of less than 400 with the other three components.

14. The method according to claim 12 further comprising reacting said polyurethane or polyurethane/polyurea with an ethylenically-unsaturated monomer.

15. The method according to claims 12, 13, or 14 further comprising the step of
   (b) effecting crosslinking of said polyurethane or polyurethane/polyurea by means of at least one of thermal energy, ultraviolet radiation, gamma radiation, and electron beam radiation.

16. A method for adjusting the crosslinking of polyurethanes or polyurethane/polyureas comprising the steps of:
   (a) providing a crosslinkable polyurethane or polyurethane/polyurea having chain extender units of the formula

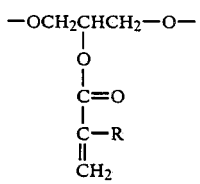

wherein R is hydrogen or methyl, and
   (b) crosslinking said polyurethane via at least one of thermal energy, ultraviolet radiation, gamma radiation or electron beam radiation.

17. The polyurethane or polyurethane/polyurea according to claim 1 wherein said macrodiol in said composition is a polyether diol, polyester diol, or silicone carbinol having the formula

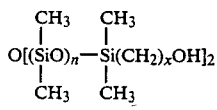

where
   n is 2 to 800, and
   x = 3 to 11.

18. The crosslinkable polyurethane or polyurethane/polyurea according to claim 2 wherein said composition further comprises at least one ethylenically-unsaturated monomer.

19. The method according to claim 13 further comprising reacting said polyurethane or polyurethane/polyurea with an ethylenically-unsaturated monomer.

20. The crosslinkable polyurethane or polyurethane/polyurea according to claim 17 wherein said composition further comprises at least one ethylenically-unsaturated monomer.

21. The polyurethane or polyurethane/polyurea according to claim 2 which has been crosslinked by means of at least one of thermal energy, ultraviolet radiation, gamma radiation, or election beam radiation.

22. The polyurethane or polyurethane/polyurea according to claim 3 which has been crosslinked by means of at least one of thermal energy, ultraviolet radiation, gamma radiation, or electron beam radiation.

23. The crosslinked polyurethane or polyurethane/polyurea according to claims 5, 19 or 20 which is a flexible magnetic recording media binder, a biomaterial, a membrane, a fabric treatment, or a protective coating.

24. The crosslinked polyurethane or polyurethane/polyurea according to claims 5, 19 or 20 which is a flexible magnetic recording media binder.

25. The crosslinked polyurethane or polyurethane/polyurea according to claims 5, 19 or 20 which is a biomaterial.

26. The crosslinked polyurethane or polyurethane/polyurea according to claims 5, 19 or 20 which is a wound dressing, a vascular graft, or an ophthalmic device.

27. The crosslinked polyurethane or polyurethane/polyurea according to claims 5, 19 or 20 which is an intraocular lens, a contact lens or a corneal implant.

28. The crosslinked polyurethane or polyurethane/polyurea according to claims 5, 19 or 20 which is a membrane.

29. The crosslinked polyurethane or polyurethane/polyurea according to claims 5, 19 or 20 which is a waterproof, breathable fabric treatment.

30. The crosslinked polyurethane or polyurethane/polyurea according to claims 5, 19 or 20 which is a protective coating.

* * * * *

UNITED STATES PATENT AND TRADEMARK OFFICE
CERTIFICATE OF CORRECTION

PATENT NO.   : 4,786,657
DATED        : November 22, 1988
INVENTOR(S)  : Hammar et al.

It is certified that error appears in the above-identified patent and that said Letters Patent is hereby corrected as shown below:

Col. 10, line 66, delete "ere" and insert therefor -- were --.

Col. 14, line 50, insert -- ) -- immediately after "(30 mmoles".

Signed and Sealed this

Fourth Day of July, 1989

Attest:

DONALD J. QUIGG

Attesting Officer

Commissioner of Patents and Trademarks